(12) United States Patent
Fukae

(10) Patent No.: US 8,020,258 B2
(45) Date of Patent: Sep. 20, 2011

(54) FIBER ACCUMULATING APPARATUS FOR ABSORBENT BODY, FIBER ACCUMULATING DRUM, AND METHOD FOR MANUFACTURING ABSORBENT BODY USING THE SAME, AND ABSORBENT ARTICLE HAVING ABSORBENT BODY MANUFACTURED BY THE METHOD

(75) Inventor: Akinori Fukae, Shikokuchuo (JP)

(73) Assignee: Daio Paper Corporation, Ehime (JP)

( * ) Notice: Subject to any disclaimer, the term of this patent is extended or adjusted under 35 U.S.C. 154(b) by 719 days.

(21) Appl. No.: 11/992,804

(22) PCT Filed: Sep. 29, 2006

(86) PCT No.: PCT/JP2006/319429
§ 371 (c)(1),
(2), (4) Date: Jun. 6, 2008

(87) PCT Pub. No.: WO2007/037357
PCT Pub. Date: Apr. 5, 2007

(65) Prior Publication Data
US 2009/0281511 A1    Nov. 12, 2009

(30) Foreign Application Priority Data

Sep. 29, 2005 (JP) .................................. 2005-283490
Sep. 29, 2005 (JP) .................................. 2005-283491
Sep. 30, 2005 (JP) .................................. 2005-286564

(51) Int. Cl.
*D01G 25/00* (2006.01)
(52) U.S. Cl. ........................................................ 19/296

(58) Field of Classification Search .................... 19/148, 19/296, 301, 308; 57/403; 264/121, 460
See application file for complete search history.

(56) References Cited

U.S. PATENT DOCUMENTS

| 3,518,726 | A  | * | 7/1970 | Banks ................ 28/121 |
| 4,666,647 | A  | * | 5/1987 | Enloe et al. .......... 264/121 |
| 4,741,941 | A  | * | 5/1988 | Englebert et al. ....... 428/71 |
| 4,761,258 | A  | * | 8/1988 | Enloe ................. 264/518 |
| 6,330,735 | B1 | * | 12/2001 | Hahn et al. ............. 19/296 |
| 6,630,088 | B1 | * | 10/2003 | Venturino et al. ....... 264/121 |
| 6,630,096 | B2 | * | 10/2003 | Venturino et al. ....... 264/518 |
| 6,846,448 | B2 | * | 1/2005 | Rymer et al. ........... 264/460 |
| 2003/0021951 | A1 | * | 1/2003 | Desai et al. ........... 428/131 |
| 2003/0116888 | A1 | * | 6/2003 | Rymer et al. ........... 264/460 |
| 2003/0132556 | A1 | * | 7/2003 | Venturino et al. ....... 264/516 |

FOREIGN PATENT DOCUMENTS

| JP | S50-109045 | 8/1975 |
| JP | S53-105573 | 9/1978 |
| JP | 07-119013  | 5/1995 |
| JP | H08-229066 | 9/1996 |

(Continued)

*Primary Examiner* — Shaun R Hurley
(74) *Attorney, Agent, or Firm* — DLA Piper LLP (US)

(57) ABSTRACT

A fiber accumulating apparatus capable of suppressing the deviation of the weight of an absorbent body by stabilizing the profile of the absorbent body and a manufacturing method for the fiber accumulating apparatus. The fiber accumulating apparatus including a fiber accumulating drum having a perforated body that accumulates an absorbent body raw material on its surface by suction from the internal side. The perforated body has a large number of sucking pores formed therein and comprises a perforated plate making up the surface and a flow-adjuster that is disposed on the internal side of the perforated plate and flow-adjusts an air flow. The perforated plate and flow-adjuster are integrally constructed.

12 Claims, 15 Drawing Sheets

FOREIGN PATENT DOCUMENTS

| | | |
|---|---|---|
| JP | 2000-234255 | 8/2000 |
| JP | 2002-272782 | 9/2002 |
| JP | 2003-507586 | 2/2003 |
| JP | 2004-65930 | 3/2004 |
| JP | 2004-530799 | 10/2004 |
| JP | 2004-222774 | 12/2004 |
| JP | 2007-054219 | 3/2007 |
| WO | WO 03/059233 | 7/2003 |

* cited by examiner

FIBER ACCUMULATING APPARATUS FOR ABSORBENT BODY, FIBER ACCUMULATING DRUM, AND METHOD FOR MANUFACTURING ABSORBENT BODY USING THE SAME, AND ABSORBENT ARTICLE HAVING ABSORBENT BODY MANUFACTURED BY THE METHOD

TECHNICAL FIELD

The present invention relates to a fiber accumulating apparatus and a fiber accumulating drum, for an absorbent body used for a paper diaper, a sanitary napkin and the like, a method for manufacturing an absorbent body using the same, and an absorbent article having an absorbent body manufactured by the method.

BACKGROUND ART

First and Second Background Arts

Absorbent bodies for absorbing urine, feces, menses or the like are used for absorbent articles such as paper diapers and sanitary napkins, and the absorbent body is formed by accumulation of fluff pulp and high water absorptive polymer.

The absorbent body is manufactured, for example, by an absorbent body manufacturing apparatus illustrated in FIG. 1. The absorbent body manufacturing apparatus includes a fluffer 51 for finely pulverizing a pulp material to be supplied, a casing 52 for surrounding the fluffer 51 and also conveying a pulverized fluff pulp using air, and a fiber accumulating apparatus 53 disposed in an opening downstream of the casing 52.

Among these, the fiber accumulating apparatus 53, as shown in FIG. 2, includes a fiber accumulating drum 30 including a mesh 32 having a large number of sucking pores formed in its outer peripheral surface and a sucking chamber 31 disposed on internal side of the fiber accumulating drum 30. The inside of the sucking chamber 31 is maintained at a negative pressure by sucking means (not shown) to thereby accumulate the fluff pulp conveyed by air on the mesh 32. The mesh 32 is attached to a reinforcing ring 34 and an absorbent body raw material S made of fluff pulp and high water absorptive polymer is accumulated in a concave portion having, as side portions, pattern rings 33, 33 disposed at both the ends of the fiber accumulating drum 30 in a transverse direction and the mesh 32 as a bottom portion.

In addition, the casing 52 is provided with a polymer loading port 54 for feeding powdered particulates of the high absorptive polymer together with the fluff pulp. Below the fiber accumulating drum 30, as shown in FIG. 1, provided is a conveyer 55 with a sucking device that transfers and conveys an absorbent body adsorbed on and held by the fiber accumulating drum 30.

Here, Patent Document 1 describes a fiber accumulating drum that suppresses the deviation of the weight of an absorbent body by means of sucking means in association with vacuum air (see Patent Document 1).

Third Background Art

Absorbent bodies for absorbing urine, feces, menses or the like are used for absorbent articles such as paper diapers, sanitary napkins and wipes. Such an absorbent body is produced by a manufacturing apparatus 201 illustrated, for example, in FIG. 15. The manufacturing apparatus for an absorbent body includes a fluffer 204 for finely pulverizing a pulp material 200 to be supplied, a fluff pulp feeding casing 208 for surrounding the fluffer, and a fiber accumulating drum 210 disposed in an opening downstream of the fluff pulp feeding casing 208. The fluff pulp feeding casing 208 constitutes the exterior cladding of a chamber C for conveying on an air flow the pulverized fluff pulp to the outer peripheral surface of the downstream fiber accumulating drum.

The fluff pulp feeding casing 208 includes a polymer loading port 206 for feeding an absorptive polymer other than the fluff pulp into the chamber. In addition, the fiber accumulating drum 210 has, at appropriate intervals in its outer peripheral surface, absorbent body-forming air-permeable concave portions. Entire surface of each concave portion is made of a fine mesh or is provided with many fine pores. The fiber accumulating drum 210 is configured so as to accumulate the fluff pulp air-conveyed in the absorbent body-forming concave portion while the fluff pulp is mixed with the absorptive polymer by maintaining the inside of the fiber accumulating drum 210 at a negative pressure by means of sucking means (not shown).

An absorbent body K' fabricated in the fiber accumulating drum 210 is transferred onto the top surface of crepe paper 250 conveyed on a vacuum conveyer by suction with a sucking device 249 and directly sent to a downstream processing step while being conveyed on the conveyer.

Here, for the purpose of improvement of absorption performance or anti-leak performance in an absorbent body for absorbing urine, feces, menses or the like, used for absorbent articles particularly such as paper diapers and sanitary napkins, when the absorbent body is used as a product, an absorbent body having a concave portion corresponding to a urination organ, a defecation organ or the like or a hole-made absorbent body having a hole portion corresponding to a defecation organ or the like may be frequently used.

Such an absorbent body or the like having a concave portion has been conventionally manufactured as follows. For example, a an absorbent body-forming concave portion of a fiber accumulating drum is sealed partly using an adhesive sheet such that fluff pulp or the like is not accumulated only there; a cone-shaped concave portion or the like is formed in an accumulated absorbent body with a convex portion such as a substantially dome protruded to a drum outer peripheral surface side by partly press molding an absorbent body-forming concave portion of the fiber accumulating drum; or alternatively, a cone-shaped concave portion or the like is formed in an accumulated absorbent body with a convex portion protruded to a drum outer peripheral surface side by partly weld-bonding a substantially bowl-shaped member to an absorbent body-forming concave portion of the fiber accumulating drum (see Patent Document 2).

Patent Document 1: Japanese Patent Laid-Open No. 2004-2227774

Patent Document 2: Japanese Patent Laid-Open No. 2002-272782

DISCLOSURE OF THE INVENTION

Problems to be Solved by the Invention

<First Problem to be Solved by the Invention>

The invention described in Patent Document 1 does not have a mechanism for flow-adjusting vacuum air by sucking means, and thus, vacuum air is left to be in an eddy flow. Because of this, it is configured so that the vacuum air is made to approach a rectified flow to suppress the deviation of the weight of the absorbent body by a method for decreasing step by step the diameter of a sucking pore of a mesh in a transverse direction. However, in such a sucking pore, clogging of fluff pulp and high water absorptive polymer to its mesh is liable to occur, whereby the profile of the absorbent body becomes unstable.

Now, for the stabilization of the profile of the absorbent body, the time needed for fiber accumulation needs to be elongated; therefore, there is a problem in that the speed in a production line is enforced to be low. In addition, the mesh clogged needs to be frequently water washed.

Further, the mesh itself is distorted by the suction force of vacuum air, thereby also posing the problem of instabilizing the profile of the absorbent body.

Hence, a first primary object of the present invention is to solve the above problem and thus is to provide a fiber accumulating apparatus for an absorbent body for stabilizing the profile of an absorbent body to thereby suppress the deviation of the absorbent body weight, a method for manufacturing an absorbent body using the apparatus, and an absorbent article having an absorbent body produced by the manufacturing method.

<Second Problem to be Solved by the Invention>

In the invention described in Patent Document 1, the mesh pore has been generally processed by cylindrical punching, so that a large amount of loss of a raw material is caused due to its passage to the inside of the fiber accumulating drum, and the mesh needs to be frequently water washed due to the clogging of high absorptive polymer.

On the other hand, since the opening ratio of the mesh is low of less than 30% and the number of pores per area is small, the vacuum air is liable to become an eddy flow, thereby creating the problem of being incapable of fine and uniform fiber accumulation.

Now, a secondary main object of the present invention is to provide a fiber accumulating apparatus for an absorbent body that hardly generates pulp break or unevenness during fiber accumulation and is capable of stabilizing the profile of cellulose wadding to decrease the deviation of the weight, and a method for manufacturing an absorbent body using the apparatus, and an absorbent article produced by the apparatus.

<Third Problem to be Solved by the Invention>

In the invention described in Patent Document 2, in the method for partly sealing the absorbent body-forming concave portion of the fiber accumulating drum, the sealed portion does not have sufficient height. For this reason, the sealed portion is prone to be buried in the fluff pulp or the like accumulated therearound, a good sterically shaped concave portion can be hardly obtained, and also the quality of a product produced therefrom may deviate. In partly press molding the absorbent body-forming concave portion so as to form a convex portion, it is unavoidable to generate stretching or breakage of fine pores of a pressed portion by the pressing. For this reason, the loss of particulate collection of the fluff pulp or polymer is generated in some cases, and thereby the weight of the resulting absorbent body is deviated, which causes unstable product profile. Additionally, in weld-bonding the bowl-shaped convex member to a portion of the absorbent body-forming concave portion, an advanced welding technology is required and also a drum producing cost is increased. Moreover, in forming the convex portion in or to a portion of the absorbent body-forming concave portion by press-molding or weld-bonding, the fiber accumulating drum producing cost is increased and further such a fiber accumulating drum cannot have general purpose properties. For example, the position of a concave portion to be formed in an absorbent body cannot be altered or an absorbent body with no concave portion cannot be produced, with this fiber accumulating drum, resulting in disadvantage Now, a third main object of the present invention is to provide a fiber accumulating drum that easily forms a predetermined shaped concave portion and is capable of readily altering the shape or position of a concave portion in an absorbent body and further of decreasing the deviation of product quality. In addition, another object is to provide a method for manufacturing an absorbent body having a good, predetermined shaped concave portion and an absorbent body obtained by the manufacturing method.

Means for Solving the Problems

The present invention for solving the above problems is in the following.

The invention is a fiber accumulating apparatus comprising a fiber accumulating drum having a perforated body that accumulates an absorbent body raw material on its surface by suction from the internal side, wherein the perforated body has a large number of sucking pores formed therein, and includes a perforated plate making up the surface and a flow-adjuster that is disposed on the internal side of the perforated plate and flow-adjusts an air flow, and the perforated plate and flow-adjuster are integrally constructed.

The invention is the fiber accumulating apparatus for an absorbent body, wherein the flow-adjuster is formed in a honeycomb structure.

(Function and Effect)

A perforated body has a large number of sucking pores formed therein and includes a perforated plate making up the surface and a flow-adjuster that is disposed on the internal side of the perforated plate and flow-adjusts an air flow, and these perforated plate and the flow-adjuster are integrally constructed. With this configuration, the vacuum air within the fiber accumulating drum can be flow-adjusted, so that the deviation of the weight of an absorbent body is small to enable fine fiber accumulation, and thus the profile of the entire cellulose wadding can be stabilized. This makes it possible to increase the rotational speed of the fiber accumulating drum and consequently to improve the production efficiency.

In addition, the construction of a flow-adjuster integrated with a perforated plate using a honeycomb structure can increase rigidity and hardly distorts the perforated plate, whereby the accumulation of the entire cellulose wadding can be made uniform.

The invention is the fiber accumulating apparatus for an absorbent body, wherein the sucking pores of the perforated plate are formed in a cone shape toward the internal side from the external side.

(Function and Effect)

The formation of sucking pores of a perforated plate in a cone shape toward the internal side from the external side can prevent an absorbent body raw material to be sucked (fluff pulp and high water absorptive polymer) from passing into the inside to thereby reduce the loss of the raw material, without complete fitting of the absorbent body raw material in the sucking pores. On the other hand, when an absorbent body is transferred from a fiber accumulating drum to a transfer drum, conveyer means, or the like as a next step, the absorbent body is transferred from an external side having a large pore size. As a consequence, the pulp or polymer left within sucking pores is moved toward the external side having a large pore size by centrifugal force due to the rotation of the drum and then discharged to the outside of the pores. Then, frequent water washing of a perforated body can be eliminated.

This can suppress clogging or the like of fluff pulp of powder particulates having different particle sizes and shapes and high water absorptive polymer. Accordingly, homogeneous vacuum force can be applied, pulp loss or unevenness during fiber accumulation hardly occurs, extremely fine fiber accumulation is made possible, the profile of cellulose wadding can be stabilized, and the deviation of the weight can be decreased.

The invention is the fiber accumulating apparatus for an absorbent body, wherein a convex member protruded in a direction away from the fiber accumulating drum is detachably provided in a portion of an absorbent body-forming concave portion in which the perforated plate is formed as a bottom portion.

(Function and Effect)

Because a convex member is detachably provided, production is possible in such a manner that the convex member can be disposed only during the production of an absorbent body having a concave portion or the like, so that the general purpose properties of the fiber accumulation apparatus can be ensured. Moreover, an appropriate alteration of the position of a convex member enables the position of a concave portion or the like in an absorbent body to be changed.

The invention is a method for manufacturing an absorbent body, wherein the fiber accumulating apparatus for an absorbent body is used.

The invention is an absorbent article having an absorbent body produced by the manufacturing method described in an embodiment.

The invention is a fiber accumulating apparatus for an absorbent body, comprising a fiber accumulating drum having a perforated body in which a large number of sucking pores are formed and an absorbent body raw material is accumulated on its surface by suction from the internal side, wherein the sucking pore of the perforated body is formed in a cone shape from the external side toward the internal side.

The invention is the fiber accumulating apparatus for an absorbent body, wherein the pore size of the sucking pore on the external side is 0.5 mm or less, and the pore size on the internal side is smaller than the pore size on the external side.

The invention is the fiber accumulating apparatus for an absorbent body, wherein the opening ratio of the sucking pore on the external side is 30% or more.

The invention is the fiber accumulating apparatus for an absorbent body, wherein the shape of the sucking pore is a conic, pyramidal or funnel shape.

The invention is the fiber accumulating apparatus for an absorbent body, wherein the sucking pores are arranged alternately, in a lattice or in a grid.

(Function and Effect)

The formation of the sucking pores of an absorbent body in a cone shape from the external side toward the internal side can prevent an absorbent body raw material to be sucked (fluff pulp and high water absorptive polymer) from passing into the inside to thereby reduce the loss of the raw material, without complete fitting of the absorbent body raw material in the sucking pores. On the other hand, when an absorbent body is transferred from a fiber accumulating drum to a transfer drum, conveyer means, or the like as a next step, the absorbent body is transferred from the external side having a large pore size. For this reason, the pulp or polymer left within the sucking pores is moved to the external side having a large pore side by centrifugal force due to the rotation of the drum and discharged to the outside of the pores. Then, frequent water washing of a perforated body can be eliminated.

This can suppress clogging or the like of fluff pulp of powder particulates having different particle sizes and shapes and high water absorptive polymer. Therefore, homogeneous vacuum force can be applied, pulp loss or unevenness during fiber accumulation hardly occurs, extremely fine fiber accumulation is made possible, the profile of cellulose wadding can be stabilized, and the deviation of the weight can be decreased.

Specifically, it is preferred that the pore size of the sucking pore on the external side is set to be 0.5 mm or less (excluding 0 mm) and the pore size on the internal side is smaller than the pore size on the external side. In addition, setting the opening ratio of a sucking pore on the external side to 30% or more and thus increasing the number of pores per area renders a polymer to be hardly clogged, thereby being capable of suppressing the generation of fiber accumulation failure.

Moreover, it is more suitable that the shape of the sucking pore is made a conic, pyramidal or funnel shape, and the sucking pores are arranged alternately, in a lattice or in a grid.

The invention is a method for manufacturing an absorbent body, wherein the method uses the fiber accumulating apparatus for an absorbent body described in any one of the previous embodiments.

The invention is an absorbent article having an absorbent body produced by the manufacturing method described in the previous embodiment.

The invention is a fiber accumulating drum for accumulating a fluff pulp conveyed on an air flow onto the surface of a rotating drum by suction from an internal side to form an absorbent body, wherein a convex member protruded in the direction away from the drum is detachably provided in a portion of an absorbent body-forming air-permeable concave portion which is formed on the outer peripheral face of the drum and on which fluff pulp is substantially accumulated.

(Function and Effect)

Because a convex member is detachably provided, the production is possible in such a manner that the convex member is disposed only during the production of an absorbent body having a concave portion or the like, so that the general purpose properties of the fiber accumulation apparatus can be ensured. Moreover, an appropriate alteration of the position of a convex member enables the position of a concave portion or the like in an absorbent body to be changed.

The invention is a fiber accumulating drum, wherein the top of the convex member is located on the position protruded in a direction away from the outer peripheral surface of the drum.

(Function and Effect)

Because the top of the convex member is located in a direction away from the outer peripheral surface of the drum, a fluff pulp is hardly accumulated on the convex member, whereby the concave portion of an absorbent body is more definitely formed.

The invention is the fiber accumulating drum, wherein the convex member is air non-permeable.

(Function and Effect)

When the convex member is air non-permeable, a fluff pulp is hardly accumulated on the convex member, and the concave portion of an absorbent body is more definitely formed.

The invention is a method for manufacturing an absorbent body, wherein the fiber accumulating drum described in any one of the previous embodiments is used.

(Function and Effect)

Simply, the position of a concave portion or the like in an absorbent body can be altered as appropriate.

The invention is an absorbent body, which is produced by using the fiber accumulating drum described in any one of the previous embodiments.

(Function and Effect)

An absorbent body can be obtained in which the shape of the concave portion or the like is good.

Effects of the Invention

According to the present invention that solves the first problem, advantages such that it is possible to stabilize the profile of an absorbent body to thereby suppress the deviation of the weight of an absorbent body are provided. In addition, according to the present invention that solves the second problem, advantages such that pulp loss or unevenness is hardly generated during fiber accumulation, and it is possible to stabilize the profile of cellulose wadding to thereby reduce the deviation of the weight. Moreover, according to the present invention that solves the third problem, a predetermined shaped concave portion is easily formed, and the shape or position of a concave portion in an absorbent body can be simply altered. Further, a fiber accumulating drum capable of decreasing the deviation of product quality is provided, and also provided are a method for manufacturing an absorbent body having a good, predetermined shaped concave portion and such an absorbent body.

BEST MODE FOR CARRYING OUT THE INVENTION

Embodiments of the present invention will be described hereinafter.

The First Embodiment of the Invention for Solving the First Problem

A fiber accumulating apparatus according to the present invention includes, for example as shown in FIG. 3, a fiber accumulating drum 1 having a perforated body 10 constituted by a mesh, punching metal or the like having a large number of sucking pores 10a, 10a, . . . formed therein and a sucking chamber 2 disposed in the internal side of the fiber accumulating drum 1. The perforated body includes a perforated plate 10A forming an outer peripheral surface of the fiber accumulating drum 1. The inside of the sucking chamber 2 is maintained at a negative pressure by sucking means (not shown) to thereby accumulate an air-conveyed absorbent body raw material S including fluff pulp or high water absorptive polymer on the surface of the perforated body 10.

The perforated body 10, as illustrated in FIG. 4, is attached to pattern rings 11, 11 disposed in both ends of the fiber accumulating drum 1 in the transverse direction using bolts 12, 12, or by welding or the like. In a concave portion having the side surfaces of the pattern rings 11, 11 as side surface portions and the perforated plate 10A of being a surface of the perforated body 10 as a bottom portion, the absorbent body raw material S including fluff pulp and high water absorptive polymer is accumulated. On the basis of the fiber accumulating apparatus of the above construction, the fluff pulp and high water absorptive polymer are supplied into the concave portion having the perforated plate 10A of being the surface of the perforated body 10 as a bottom portion, and accumulated and formed in a predetermined shape within the concave portion on account of a negative pressure within the sucking chamber.

In addition, below the fiber accumulating drum, as shown in FIG. 1 described above, a conveyer 55 with a sucking device is disposed that transfers and conveys an absorbent body adsorbed on and held by the fiber accumulating drum. Because of this, an absorbent body accumulated by the sucking chamber 2 is rotated to a peripheral direction while being adsorbed on and held by the outer periphery of the fiber accumulating drum 1, transferred onto the conveyer by the sucking device when reaching the conveyer 55 with a sucking device, and directly conveyed.

A conventional fiber accumulating apparatus 53 does not have a mechanism that flow-adjusts vacuum air by sucking means and its air flow is an eddy flow. "To flow-adjust" used herein is to vacuum within the space of a casing 52 partitioned from a fluffer 51 (row powder facility) to the fiber accumulating apparatus 53 (fiber accumulating facility), and refers to a state in which while a flow of air is generated within the space, the direction of the air flow is constant in any portions within the space and the flow speed and amount by vacuum suction is also constant. As the angle of the space within the casing 52 approaches 180 degrees (horizontal), the flow becomes close to an adjusted flow. As for the distance of the space within the casing 52, the longer the distance, the more close to an adjusted flow the flow tends to be, under constant vacuum force conditions.

In conventional facilities, due to clogging of pulp and polymer to a mesh and distortion of a mesh and special problems in facilities, the distance of the space within the casing 52 cannot be kept long, and the angle is also designed and set closer to 90 degrees. Under these circumstances, the flow of air due to vacuum suction is liable to be disturbed and becomes an eddy flow.

In conventional facilities, operation is conducted in the vacuum pressure (static pressure) range of from 2400 to 5000 Pa, and under constant vacuum pressure conditions, for example, at 4000 Pa, the actual pressure is in the range of from 3600 to 4400 Pa due to an eddy flow and thus is unstable (about 10% or more of inaccuracy occurs).

Now, in a perforated body of a conventional mesh 32 illustrated in FIG. 2 or the like, a construction is adopted in which vacuum air is approached to an adjusted flow to thereby suppress the deviation of the weight of an absorbent body, by a method for decreasing step by step the diameter of the sucking pore of the mesh 32 in the transverse direction. As such, the load applied to the mesh 32 is large, and in such a sucking pore the clogging of fluff pulp and high water absorptive polymer to the mesh 32 is liable to occur; as a result, the profile of an absorbent body becomes unstable. Further, for the stabilization of the profile of an absorbent body, the timed needed for fiber accumulation needs to be elongated, so that the speed in the production line of a thin-type absorbent body is forced to be slow, leading to worsening of production efficiency. In addition, a mesh clogged needs to be frequently water washed. Moreover, the mesh itself is distorted by the suction force of vacuum air, which poses a problem in that the profile of an absorbent body is unstable.

On the other hand, the perforated body 10 according to the present invention, as illustrated in FIG. 3, is constituted by a mesh or a punching metal having a large number of perforated pores 10a, 10a, . . . formed therein. Also, the perforated body 10 includes the perforated plate 10A forming the surface and the flow-adjuster 10B constituted by a honeycomb structure disposed in the internal side (back side) of the perforated plate 10A, and the perforated plate 10A and the flow-adjuster 10B are configured so as to be integrated with each other.

The structure of the perforated body 10 in which the perforated plate 10A and the flow-adjuster 10B are integrated with each other can flow-adjust vacuum air within the fiber accumulating drum, and thus enables the absorbent body weight with a small deviation and fine fiber accumulation, whereby the profile of the entire cellulose wadding can be stabilized. This makes it possible to increase the rotational speed of a fiber accumulating drum and consequently possible to improve production efficiency. Provision of the flow-adjuster 10B leads to stabilization under constant vacuum pressure conditions, for example, at 4000 Pa, maximally in the range of from 3800 to 4200 Pa (can be suppressed to an inaccuracy of about 5% or less). In addition, because of the honeycomb structure of the flow-adjuster 10B, making this structure be integrated with the perforated plate 10A (e.g., by welding) increases rigidity, rarely distorts the perforated plate 10A and enables the accumulation of the entire cellulose wadding to be uniformed.

As a transverse cross sectional shape of the flow-adjuster 10B (layer structure), a form of the longitudinal stacking of bricks as shown in FIG. 5 can be considered. In this case, the size of a measure of the flow-adjuster 10B illustrated in FIGS. 3 and 5 may be 20 mm or less (excluding 0 mm) in the length (L) in the longitudinal direction, 20 mm or less (excluding 0 mm) in the width (W) and 20 mm or less (excluding 0 mm) in height (H). The back side and external side of the flow-adjuster 10B in this case are indicated in FIG. 7 and FIG. 8, respectively. In addition, the perforated plate 10A on the external side is not illustrated. Another form may be a bellows shape as shown in FIG. 7, or a lattice shape (not shown).

Additionally, the shape of the sucking pore 10a, 10a, . . . , of the perforated plate 10A, as sucking pores 4A, 4A indicated in FIG. 9, may be subjected to processing in which the pore size becomes small toward the inside of the fiber accumulating drum 1 and be formed in a cone shape from the external side toward the internal side.

Moreover, a convex member 110X protruding in a direction away from the fiber accumulating drum as illustrated in FIG. 14 can be detachably provided in a portion of a concave portion (an absorbent body-forming concave portion) having the perforated plate 10A of being the surface of the perforated body 10 as a bottom portion to which a fluff pulp or a high water absorptive polymer is supplied.

The Second Embodiment of the Invention for Solving the Second Problem

A fiber accumulating apparatus according to the present invention includes a fiber accumulating drum 1 having a perforated body 4 constituted by, for example as shown in FIG. 9, a mesh, punching metal or the like having a large number of sucking pores 4A, 4A, . . . formed in the outer peripheral surface of the fiber accumulating drum 1, and a sucking chamber 2 disposed in the internal side of the fiber accumulating drum 1. The inside of the sucking chamber 2 is maintained at a negative pressure by sucking means (not shown) to thereby accumulate an air-conveyed absorptive raw material S including a fluff pulp or a high water absorptive polymer on the surface of a perforated body 4.

The perforated body 4, as illustrated in FIG. 10, is attached to an auxiliary ring 13 through bolts 12, 12, and the absorptive raw material S including fluff pulp and high water absorptive polymer is accumulated in a concave portion having the side surfaces of the pattern rings 11, 11 as side surface portions, disposed in both the ends of the fiber accumulating drum 1 in the transverse direction, and a surface of the perforated body 4 as a bottom portion. On the basis of the fiber accumulating apparatus of the above construction, the fluff pulp and high water absorptive polymer are supplied to the inside of the concave portion having the surface of the perforated body 4 as a bottom portion and accumulated and formed in a predetermined shape within the concave portion on account of a negative pressure within the sucking chamber.

In addition, below the fiber accumulating drum, as shown in FIG. 1 described above, a conveyer 55 with a sucking device is disposed that transfers and conveys an absorbent body adsorbed on and held by the fiber accumulating drum. Because of this, an absorbent body accumulated by the sucking chamber 2 is rotated to a peripheral direction while being adsorbed on and held by the outer periphery of the fiber accumulating drum 1, transferred onto the conveyer by the sucking device when reaching the conveyer 55 with a sucking device, and directly conveyed.

As illustrated in FIG. 2, the conventional mesh 32 has been generally processed by cylindrical punching, so that a large amount of loss of a raw material is caused due to its passage to the inside of the fiber accumulating drum, and the mesh needs to be frequently water washed due to clogging of high absorptive polymer. However, in the present invention, since the mesh 4 has been generally processed by conic type etching an absorbent body raw material to be sucked can be prevented from passing into the inside to thereby reduce the loss of the raw material, without complete fitting of the absorbent body raw material in the sucking pores. On the other hand, when an absorbent body is transferred from the fiber accumulating drum 1 to the conveyer 55 with a sucking device as a next step, the absorbent body is transferred from the external side having a large pore size, so that the raw material is not clogged within the sucking pores 4A, 4A, . . . , and can be efficiently transferred. In addition, frequent water washing of the perforated body 4 can be eliminated.

Specifically, a cone shape is suitably formed in such a manner that the pore size of the sucking pore 4A, 4A, . . . , on the external side is set to be 0.5 mm or less (excluding 0 mm), and that the pore size of the internal size (back side) is smaller than the pore size of the external side.

On the other hand, the opening ratio of the perforated body such as the conventional mesh 32 is low of less than 30%, and the number of pores per area is small, so that the vacuum air is liable to be an eddy flow and thus there is a problem in that fine, uniform fiber accumulation cannot be conducted. However, the opening ratio of the sucking pores 4A, 4A, . . . , according to the present invention (the ratio of the total pore area of the sucking pores to the surface area of the perforated body) on the external side is set to be 30% or more, and the number of pores per area is increased, whereby a polymer is hardly clogged to thereby suppress the generation of fiber accumulation failure. Moreover, the higher the opening ratio, the more uniform the fiber accumulation is expected to be. However, when the opening ratio is too high, the strength of the perforated body is reduced, and thus is suitably set to be 70% or less.

The above construction makes it possible to suppress clogging or the like of a fluff pulp or a high water absorptive polymer, of powder particles having different particle sizes and shapes. For this reason, uniform vacuum force can be applied, pulp break or unevenness during fiber accumulation is hardly generated, fine fiber accumulation is possible, the profile of the cellulose wadding can be stabilized, and the weight deviation can be reduced.

The sucking pores 4A, 4A, . . . , in the perforated body 4 may be, as illustrated in FIG. 11, arranged alternately or in a lattice as shown in FIG. 12, or in a grid (not shown). In addition, although not shown, the pore shape may be replaced by a pyramidal or funnel shape, in place of a conic shape.

The Third Embodiment of the Invention for Solving the Third Problem

FIG. 13 is a schematic diagram of an apparatus for manufacturing an absorbent body including a fiber accumulating drum according to the present invention, and FIG. 14 is a plan view in the vicinity of its fiber accumulating drum.

An absorbent body manufacturing apparatus 101 primarily includes a fluffer for finely crushing a pulp material (pulp raw fabric) 102 to be fed, a fluff pulp feeding casing 108 surrounding the fluffer, and a fiber accumulating drum 110 placed in an opening downstream of the fluff pulp feeding casing 108. The fluff pulp feeding casing 108 constitutes the exterior cladding of a chamber C for conveying, on an air flow, the pulverized fluff pulp to the outer peripheral surface of the downstream fiber accumulating drum. In addition, the fluff pulp feeding casing 108 is provided with a functional powder feed opening 106 for feeding into the chamber a functional powder such as a polymer other than the fluff pulp, a deodorizing material, an antimicrobial material or an indicator.

The fiber accumulating drum 110 has, at appropriate intervals in its outer peripheral surface, absorbent body-forming air-permeable concave portions 110a, 110a. Entire surface of each concave portion 110a is made a fine mesh or is provided with a large number of fine pores. The fiber accumulating drum 110 is configured so as to accumulate the fluff pulp and the absorptive polymer in the absorbent body-forming concave portions 110a, 110a while the fluff pulp and the absorptive polymer are mixed with each other by maintaining the inside of the fiber accumulating drum 110 at a negative pressure by means of sucking means (not shown).

Here, in a fiber accumulating drum in the present invention, a convex member 110X protruding in a direction away from the drum is detachably provided in portions of the absorbent body-forming concave portions 110a, 110a. The convex member 110X substantially has a convex portion 110t for rendering an absorbent body to form a concave portion or a pore and an attaching portion 110h for detachably attachment to the outer peripheral surface of the drum. With the convex member 110X attached, its convex portion 110t is protruded in a direction away from the drum in a portion of the absorbent body-forming concave portion 110a, so that a concave portion or the like is formed in an absorbent body accumulated and formed in the concave portion 110a for forming an absorbent body. A specific shape of the convex portion 110t defines a shape of the concave portion or of the pore of an absorbent body. Hence, for example, if the shape of the convex portion 110t is made to be substantially a dome shape, a cone-shaped concave portion or the like is formed in an absorbent body. On the other hand, when the top of the convex portion 110t is a flat surface, an absorbent body having a concave portion with a bottom shape corresponding to the top face shape or having a pore with the corresponding shape is obtained. Although the specific position and the range of the convex portion 110t, the total convex portion size and the convex portion height within the absorbent body-forming concave portion 110a can be changed appropriately depending on a required absorbent body, for example, in the case of an absorbent body used for paper diaper applications, the position of the concave portion of the absorbent body is preferably disposed so as to be extendedly present toward the back side from the portion corresponding to a urination organ. For this reason, the convex portion is disposed so as to correspond to a position in which such a concave portion is formed, or to the like. In such applications, the area of the concave portion (flat view) is desirably made to be 1/6 or less of an absorption body area (flat view), so that the area covered with the convex member is made to be 1/6 or less of the area of the absorbent body-forming concave portion 110a. Additionally, in such applications, the depth of the concave portion of an absorbent body is desirably 10 mm or less, and therefore the height of the convex portion 110t of the convex member 110X is made to be 10 mm or less.

The method for attaching the convex member 110X to the absorbent body-forming concave portion (drum peripheral surface) 110a is not particularly limited. However, in the present embodiment, the attaching portion 110h formed with a plate spring having elasticity in the circumferential portion of the convex member 110X is formed and also a fitting groove 110m for fitting the portion in the drum outer peripheral surface is formed. It is configured that, with the attaching portion 110h bent, the brim of the attaching portion 110h is inserted into the fitting groove 110m of the drum outer peripheral surface and then the bending is stretched to thereby fit the convex member in a portion of the absorbent body-forming concave portion 110a, 110a for attaching. Moreover, for attaching the convex member to a drum outer peripheral surface, there can be a method for detachable attachment by means of other bolts and nuts, etc. and a method for detachable attachment by adhesion.

Here, in the present embodiment, with the convex member 110X attached to the drum peripheral surface, the top of its convex portion 110t is located in a position protruded in a direction away from the drum outer peripheral surface. In other words, the height of the convex portion 110t is set to be larger than the depth of the absorbent body-forming concave portion 110a. This definitely prevents deposition of pulp and the like in the convex portion and forms a predetermined, good shaped concave portion or an absorbent body having a pore portion.

Furthermore, although a convex member can also be formed using a material having a fine air-permeable pore such as a mesh material or a punching metal, it is actually formed with a nonporous non-air-permeable material in the present embodiment. This ensures more definitely pulp or the like not to be accumulated in the convex member attaching portion, resulting in a good shaped concave portion or pore of an absorbent body as intended.

Here, the above sucking means is configured so as to enable accumulation of the fluff pulp 7 and polymer P on the absorbent body-forming concave portion 110a, 110a, . . . in a width substantially over a fiber accumulation range of the fiber accumulating drum, as well as to enable formation of a negative pressure generating suction region 110A (symbol −) for the purpose of conveying an absorbent body S formed and adsorbed and formation of an air supplying region 110B (symbol +) of supplying air to generate a positive pressure for the purpose of transferring the absorbent body S to a conveyer 115 with a sucking device as described below. It is configured so that the fluff pulp 107 and the polymer P accumulated on the absorbent body-forming concave portion 110a of the fiber accumulating drum 110 are conveyed in a peripheral direction A (clockwise direction) while being adsorbed and held by suction and, when reaching the air supplying region 110B, transferred to the side of the conveyer 115 with the sucking device.

The conveyer 115 with the sucking device receiving an absorbent body K from the fiber accumulating drum 110 is a conveyer that makes an air-permeable conveyer belt 118 hang over between rollers 116, 117 and arranges a receiving roller 119 in an appropriate place, with a structure in which the air-permeable conveyer belt 118 is put between the fiber accumulating drum 110 and a sucking device 120 placed in a downstream position thereof. To this the conveyer 115 with the sucking device, supplied is crepe paper 121 to cover the undersurface side of the absorbent body K through guide rollers 122a to 122d and the absorbent body K is laminated on the above crepe paper 121.

In this manner, the absorbent body K having a concave portion or a pore portion formed therein by means of a convex member is conveyed downstream together with the crepe paper 121 and then passed through appropriate steps to be processed to an individual absorbent body unit.

EXPLANATION OF REFERENCE NUMERALS

Figure 1:
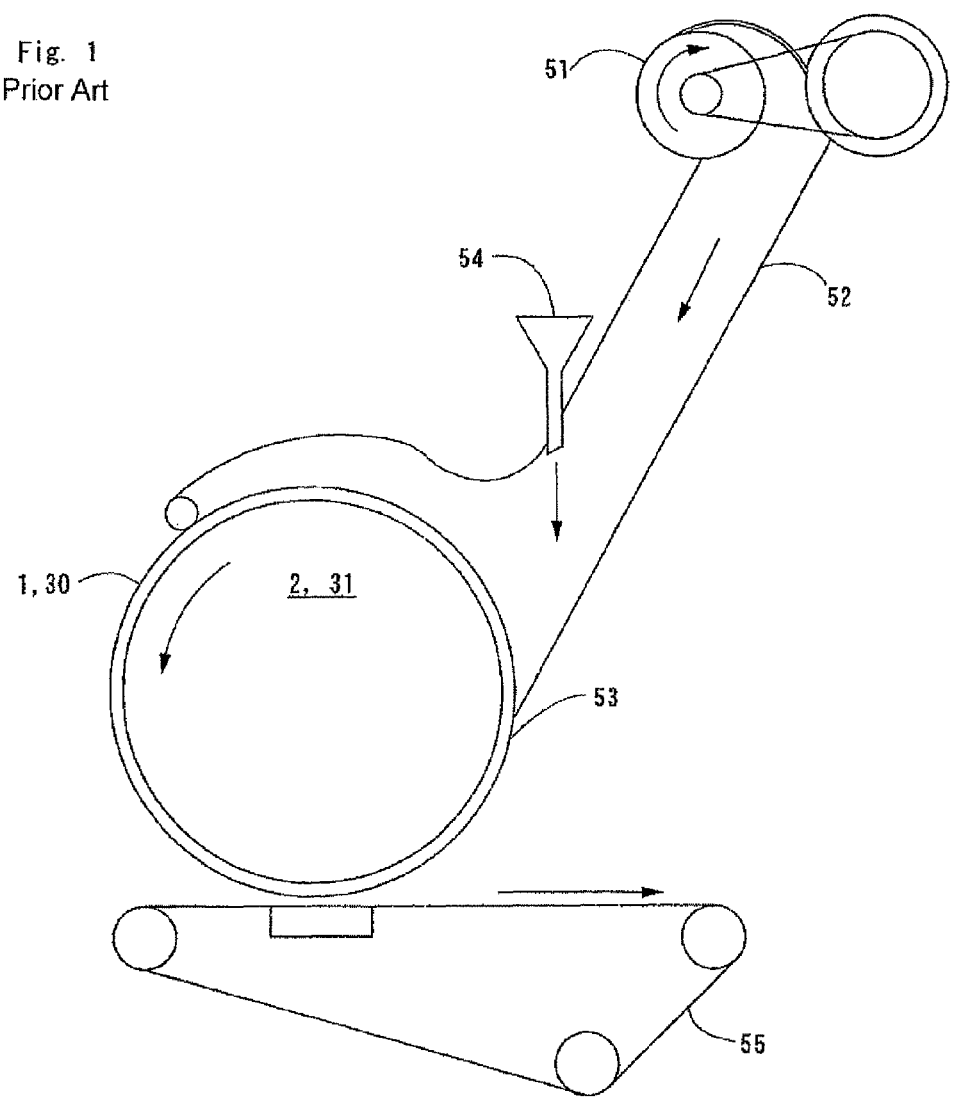
FIG. 1 is a schematic diagram of an apparatus for manufacturing an absorbent body.
Figure 2:
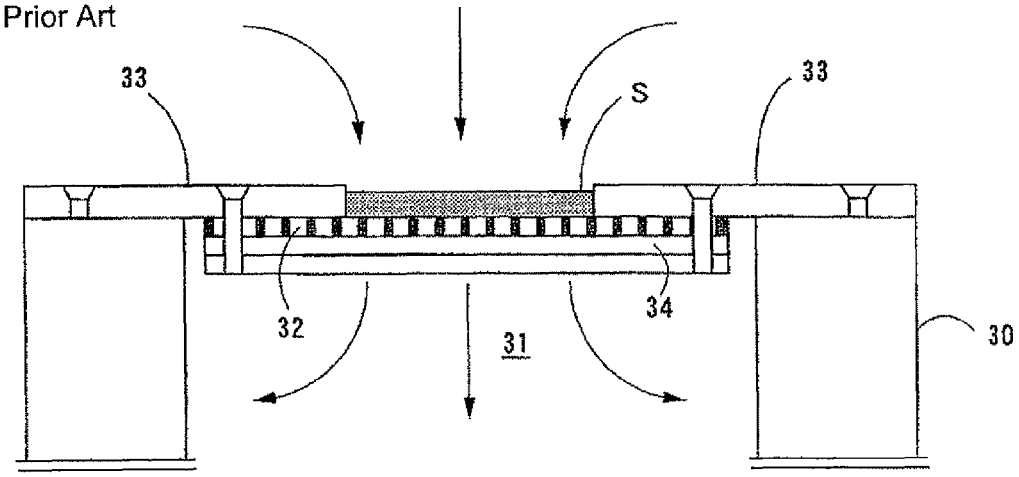
FIG. 2 is an enlarged sectional view of a fiber accumulating drum of a conventional example.
Figure 3:
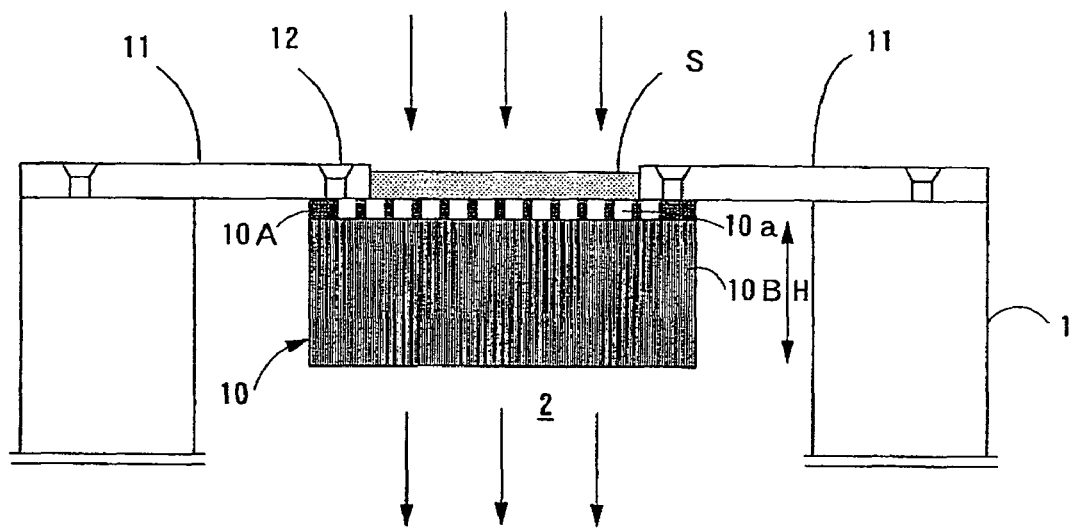
FIG. 3 is a partial sectional view of a fiber accumulating drum according to the present invention for solving a first problem.
Figure 4:
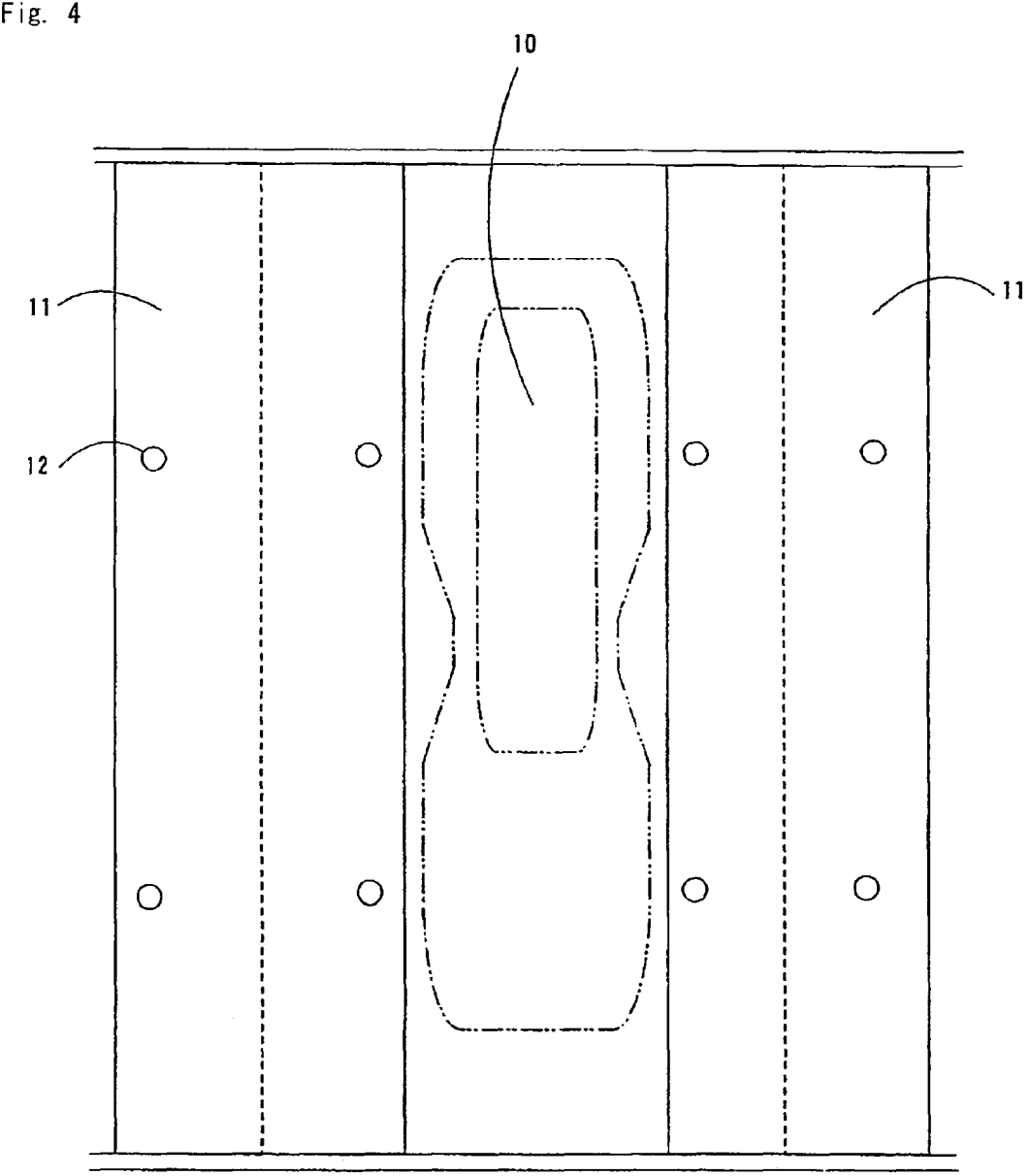
FIG. 4 is a partial plan view of the fiber accumulating drum.
Figure 5:
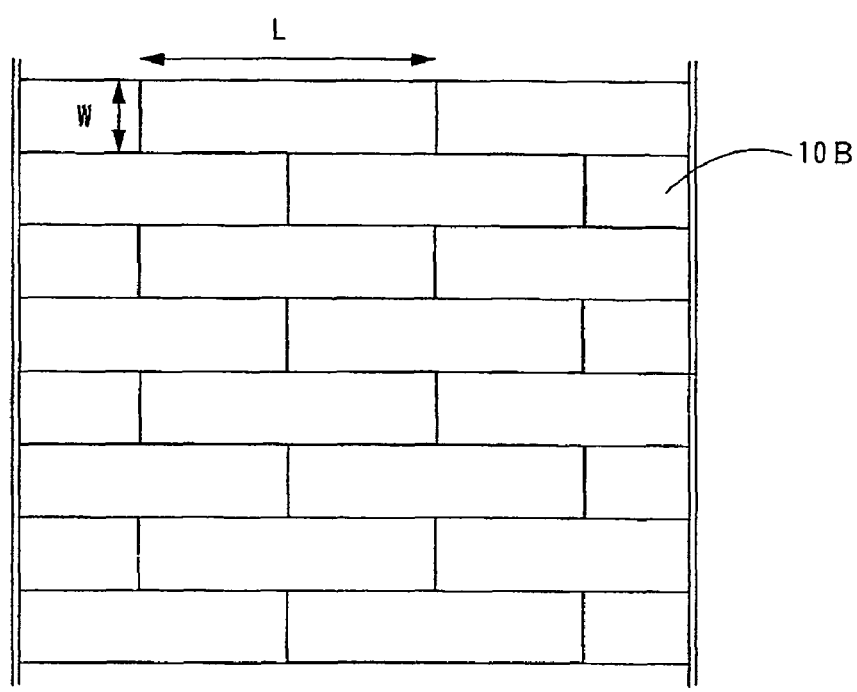
FIG. 5 is a schematic diagram of a transverse cross section of a flow-adjuster.
Figure 6:
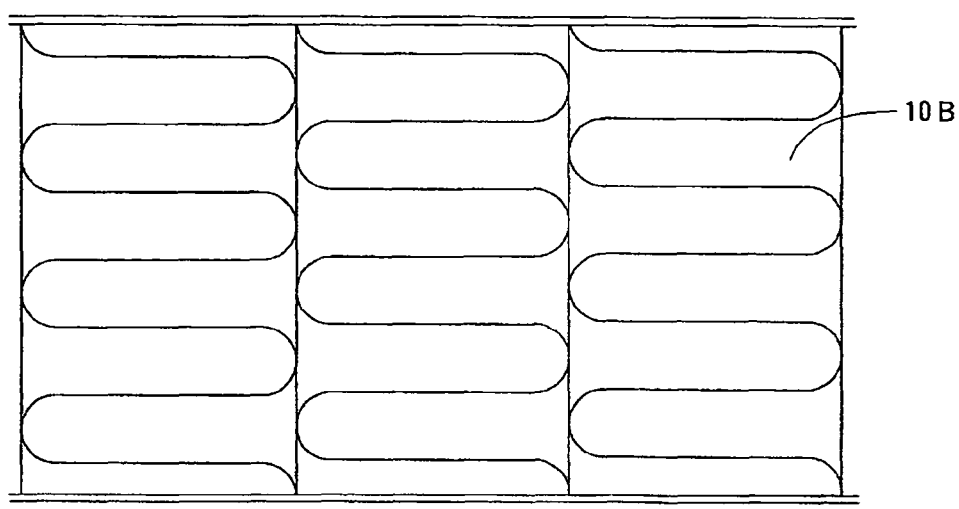
FIG. 6 is a schematic diagram of a transverse cross section of another flow-adjuster.
Figure 7:
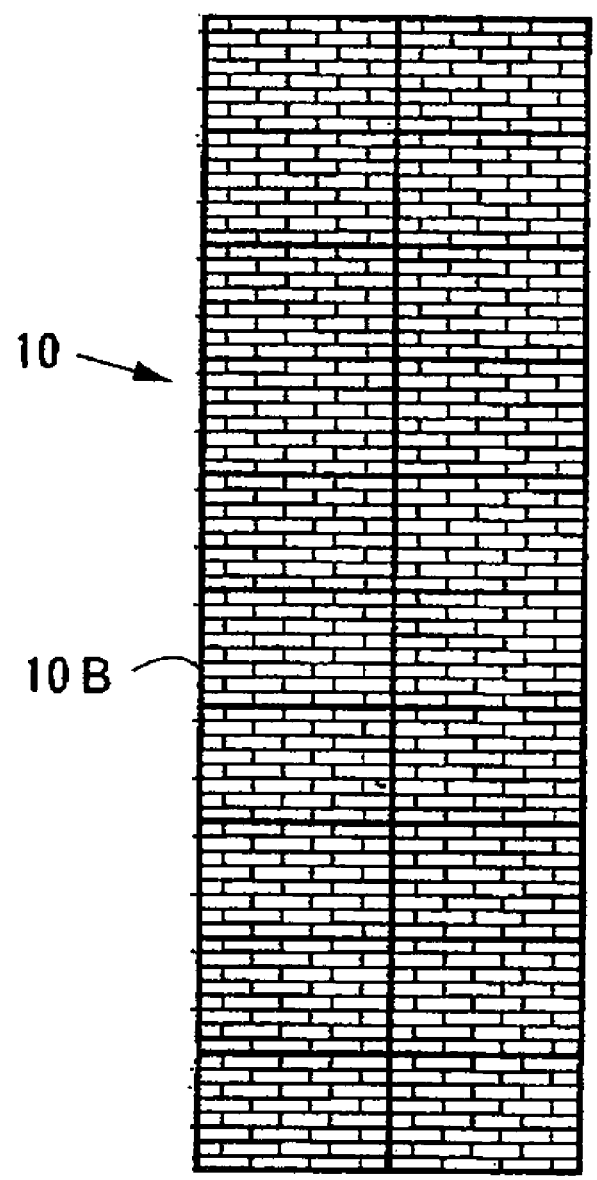
FIG. 7 is a schematic diagram viewed from a back side of a transverse cross section of a flow-adjuster.
Figure 8:
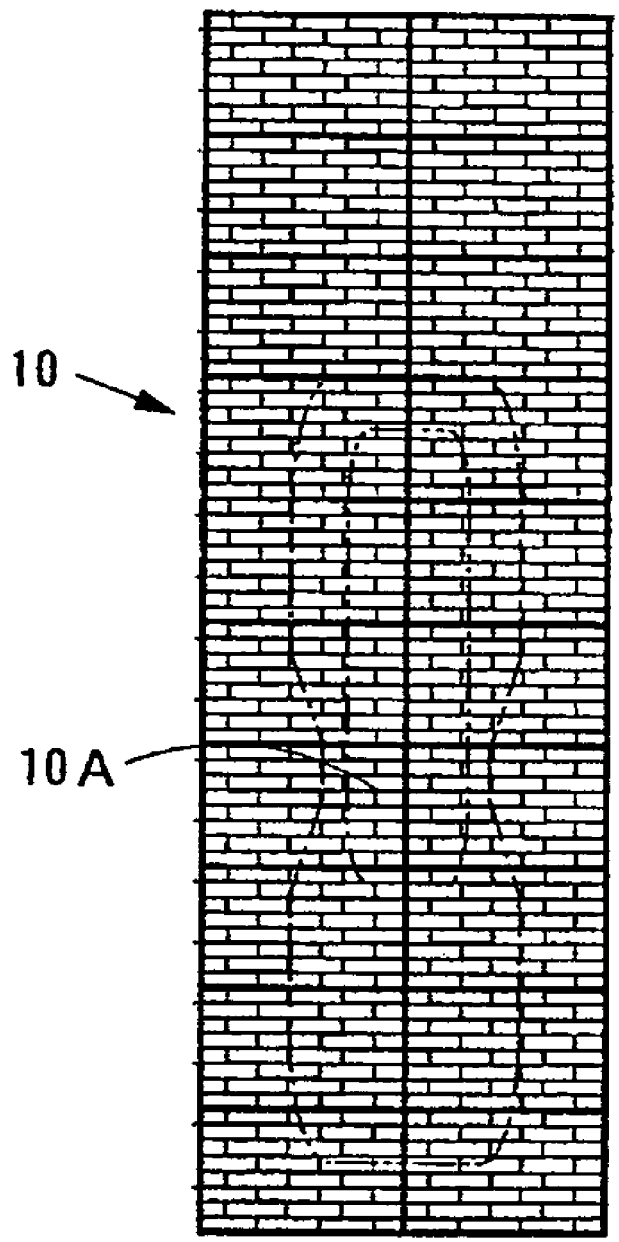
FIG. 8 is a schematic diagram viewed from a front side of the transverse cross section of the flow-adjuster.
Figure 9:
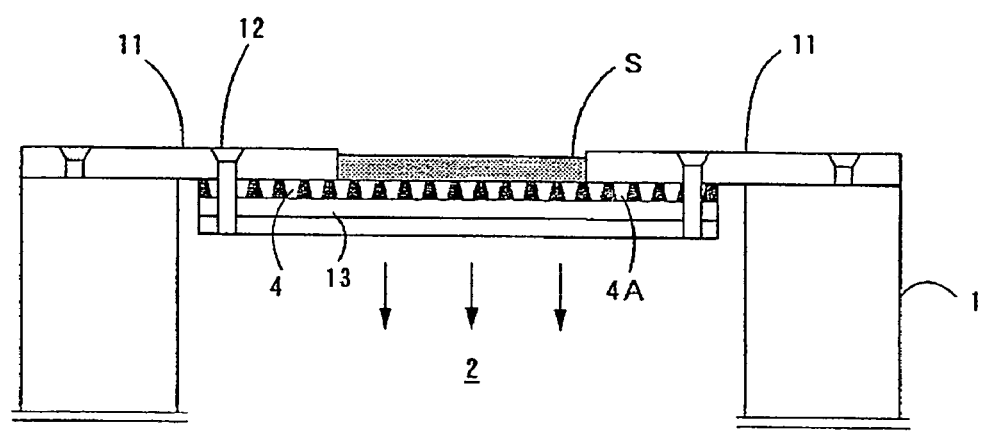
FIG. 9 is a partial sectional view of a fiber accumulating drum according to the present invention for solving a second problem.
Figure 10:
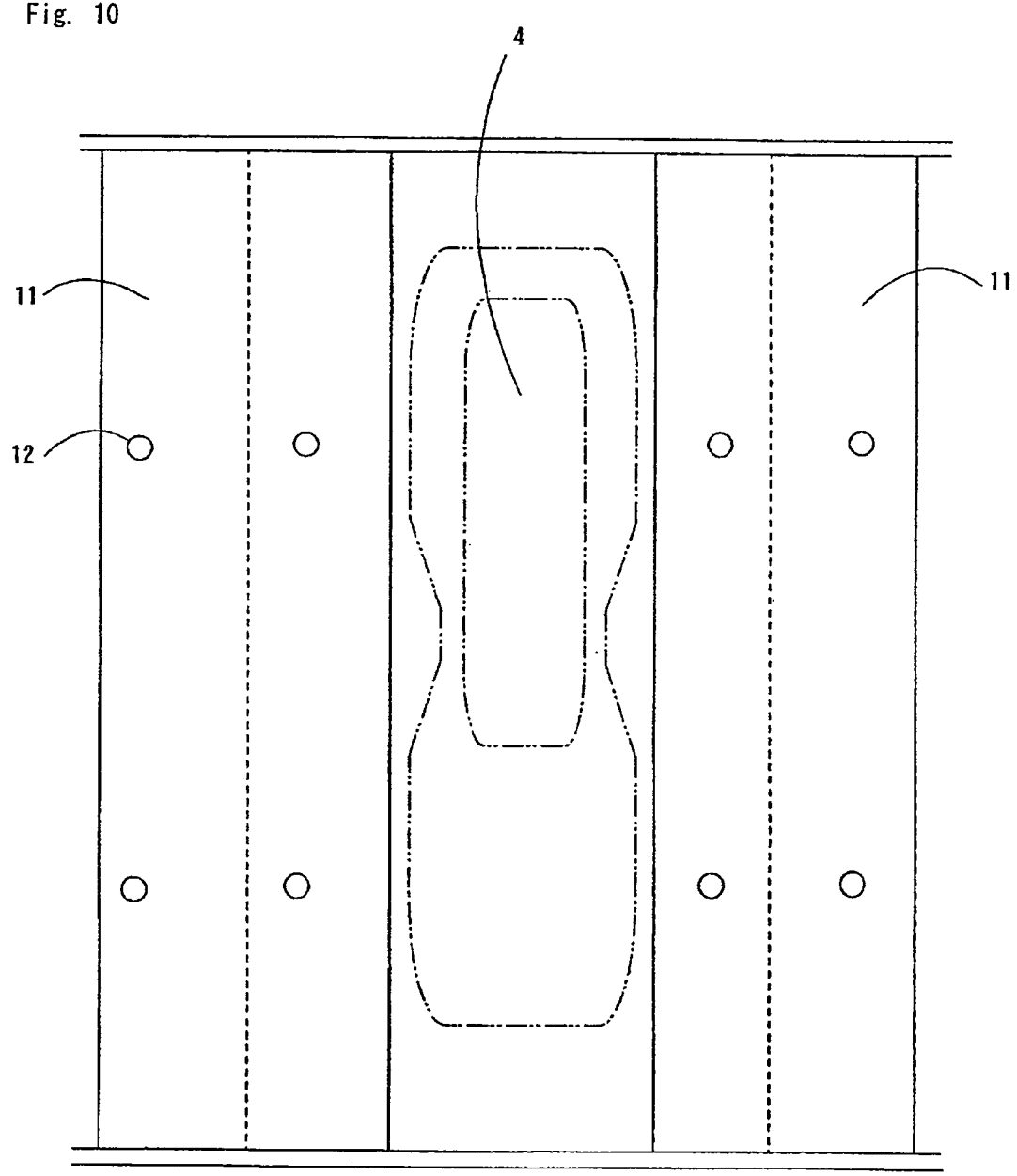
FIG. 10 is a partial plan view of the fiber accumulating drum.
Figure 11:
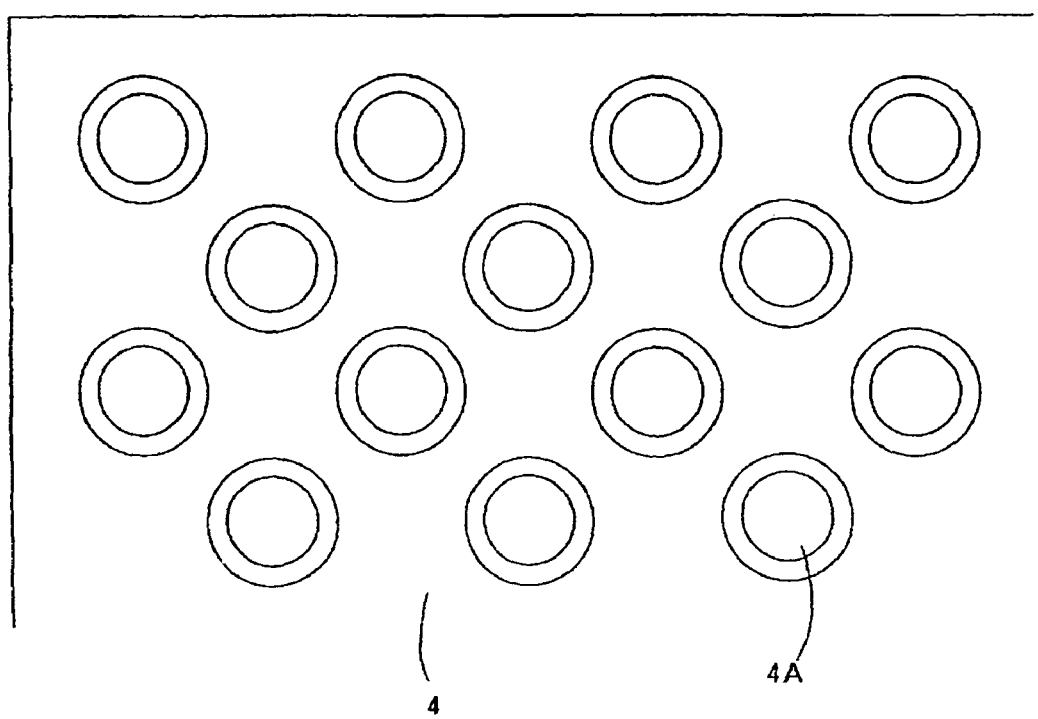
FIG. 11 is a schematic diagram indicating an arrangement of sucking pores.
Figure 12:
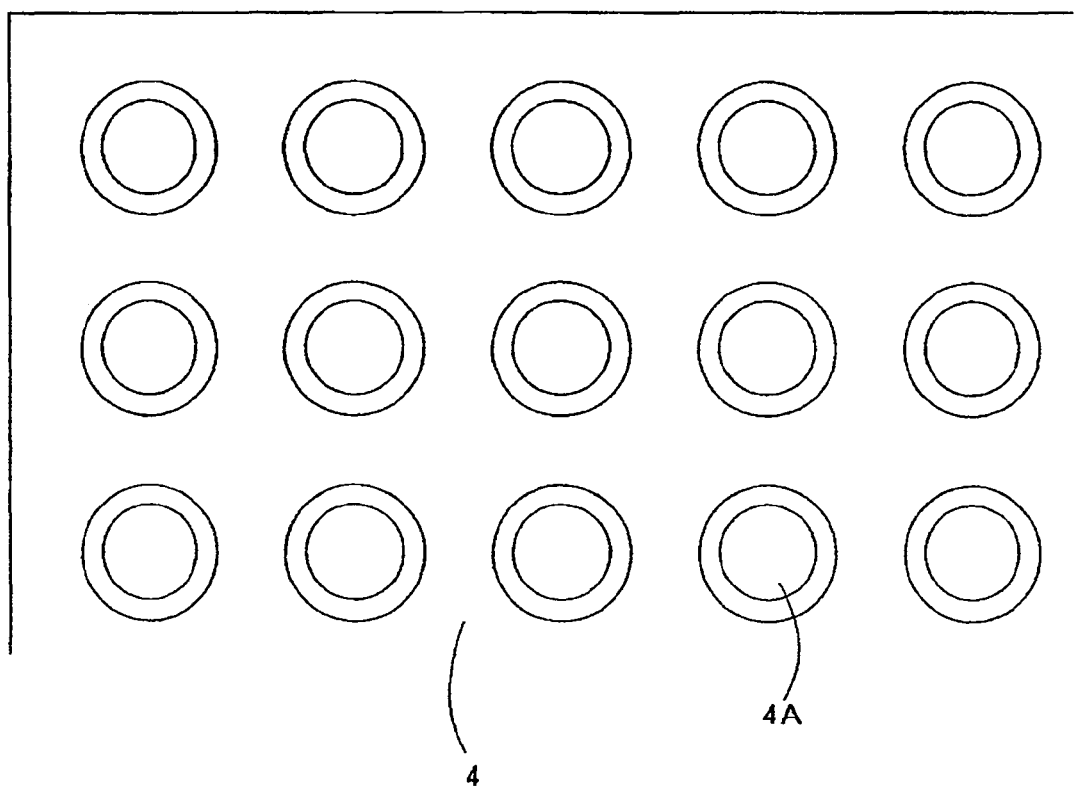
FIG. 12 is a schematic diagram indicating another arrangement of sucking pores.
Figure 13:
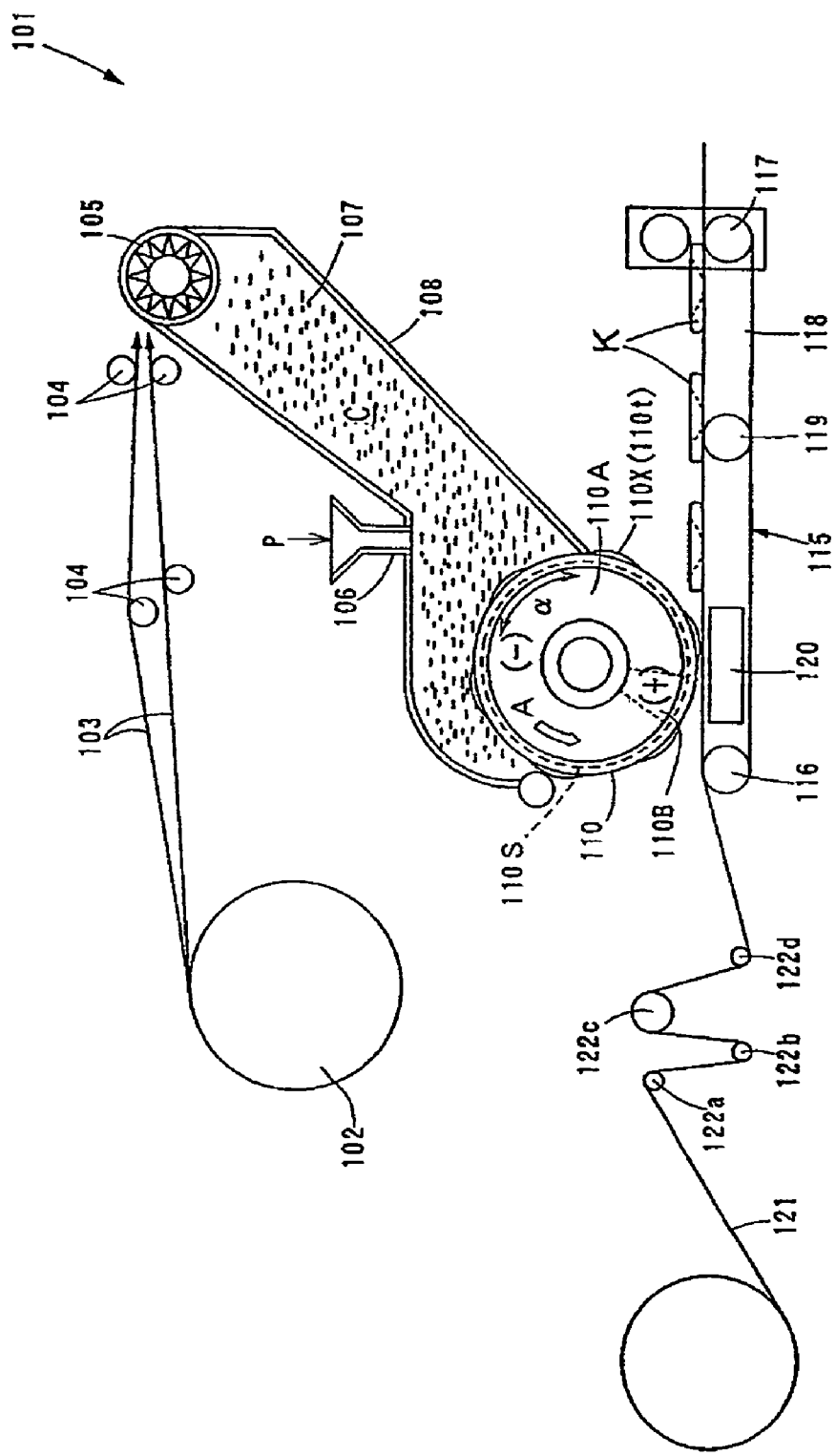
FIG. 13 is a schematic diagram of an apparatus for manufacturing an absorbent body according to the present embodiment of solving a third problem.
Figure 14:
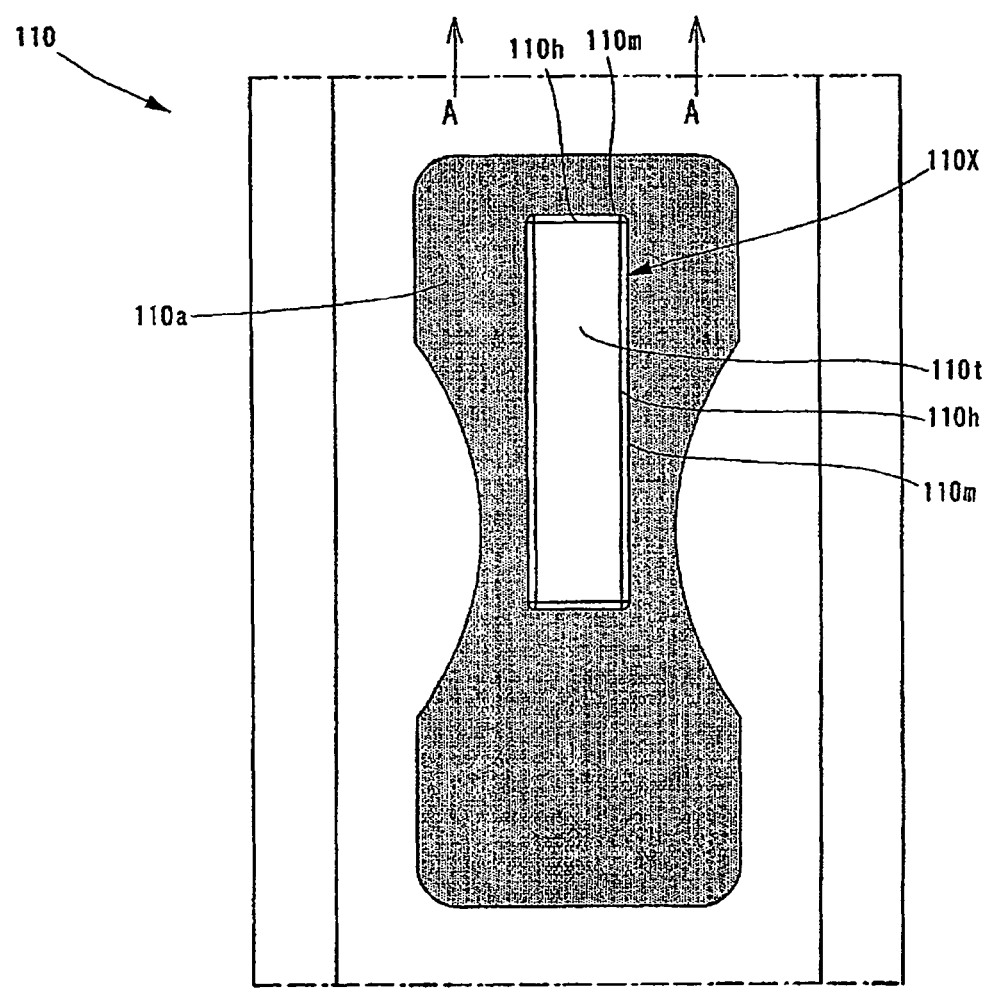
FIG. 14 is a plan view in the vicinity of the fiber accumulating drum.
Figure 15:
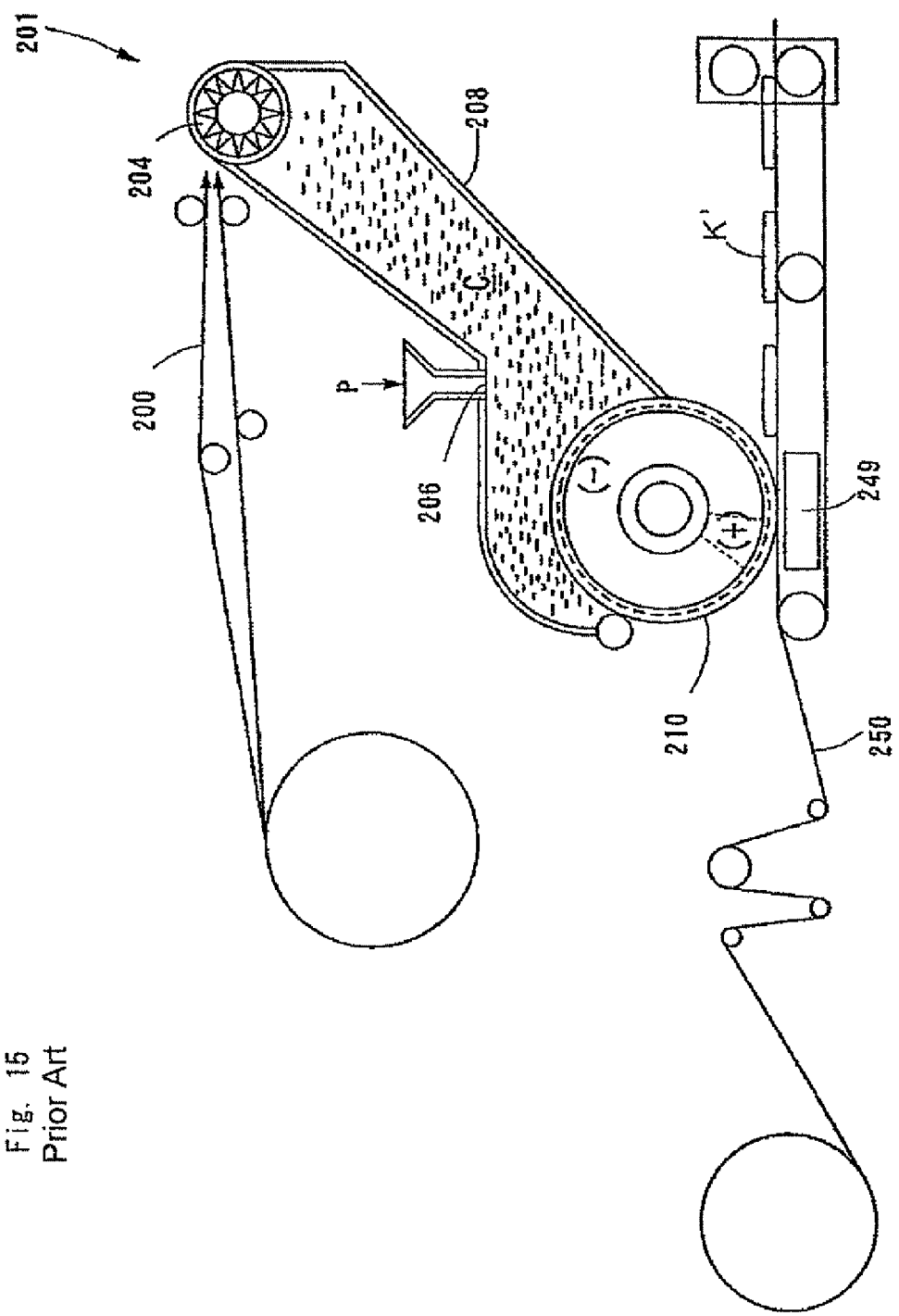
FIG. 15 is a schematic view of a conventional apparatus for manufacturing an absorbent body.

1 fiber accumulating drum
2 sucking chamber
4 perforated body
4A sucking pore
10 perforated body
10A sucking plate
10B flow-adjuster
10a sucking pore
11 pattern ring
12 bolt
S absorbent body raw material
101 absorbent body manufacturing apparatus
102 pulp material (pulp raw fabric)
103 pulp paper material
105 fluffer
106 functional powder feed opening
107 fluff pulp
108 fluff pulp feeding casing
110 fiber accumulating drum
110A suction region
110B air supplying region
110a absorbent body-forming concave portion
110X convex member
110t convex portion
110h attaching portion
110m convex member fitting groove
115 conveyer with sucking device
116, 117 roller
118 air-permeable conveyer belt
119 roller
120 sucking device
122a to 122d guide roller
121 crepe paper

The invention claimed is:

1. A fiber accumulating apparatus for an absorbent body of an absorbent article, comprising a fiber accumulating drum having on an outer peripheral surface thereof a concave portion having a shape that corresponds to a shape of an absorbent body of an absorbent article, wherein said fiber accumulating drum is provided with a perforated body that forms a bottom of said concave portion, said perforated body is formed with a large number of sucking pores that open to said bottom of said concave portion; and while said fiber accumulating drum is being rotated and suctioning is being made from said sucking pores toward internal side of said fiber accumulating drum, an air-conveyed absorbent body raw material including fluff pulp and high water absorptive polymer is directly accumulated on said perforated body which is within said concave portion, and the accumulated absorbent body raw material is transferred onto a transferring conveyor provided so as to face said fiber accumulating drum, thus forming the absorbent body raw material into an absorbent body of an absorbent article; and wherein said perforated body has said large number of sucking pores formed therein and comprises a perforated plate that makes up said bottom of said concave portion and a flow-adjuster that is disposed on an internal side of said perforated plate and flow-adjusts an air flow, said perforated plate and said flow-adjuster are integrally constructed; and each of said sucking pores of said perforated body is formed in a cone shape having pore sizes in diameter smaller on an internal side than on an external side thereof so as to prevent said absorbent body raw material from completely fitting in said sucking pores or from passing into an inside of said fiber accumulating drum.

2. The fiber accumulating apparatus for an absorbent body of an absorbent article according to claim 1, wherein said flow-adjuster is formed in a honeycomb structure.

3. The fiber accumulating apparatus for an absorbent body of an absorbent article according to claim 1, wherein an air non-permeable convex member protruded in a direction away from the fiber accumulating drum is detachably provided in a part of said bottom of said concave portion.

4. A method for manufacturing an absorbent body of an absorbent article, wherein the fiber accumulating apparatus for an absorbent body of claim 1 is used.

5. A fiber accumulating apparatus for an absorbent body of an absorbent article, comprising a fiber accumulating drum having on an outer peripheral surface thereof a concave portion having a shape that corresponds to a shape of an absorbent body of an absorbent article, wherein said fiber accumulating drum is provided with a perforated body that forms a bottom of said concave portion, said perforated body is formed with a large number of sucking pores that open to said bottom of said concave portion; and while said fiber accumulating drum is being rotated and suctioning is being made from said sucking pores toward internal side of said fiber accumulating drum, an air-conveyed absorbent body raw material including fluff pulp and high water absorptive polymer is directly accumulated on said perforated body which is within said concave portion, and the accumulated absorbent body raw material is transferred onto a transferring conveyor provided so as to face said fiber accumulating drum, thus forming the absorbent body raw material into an absorbent body of an absorbent article; and wherein each of said sucking pores of said perforated body is formed in a cone shape having pore sizes in diameter smaller on an internal side than on an external side thereof so as to prevent said absorbent body raw material from completely fitting in said sucking pores or from passing into an inside of said fiber accumulating drum.

6. The fiber accumulating apparatus for an absorbent body of an absorbent article according to claim 5, wherein the pore size of each of said sucking pores on the external side is 0.5 mm or less, and the pore size on said internal side is smaller than the pore size on said external side.

7. The fiber accumulating apparatus for an absorbent body of an absorbent article according to claim 5, wherein an opening ratio, which is a ratio of total pore area of said sucking pores on the external side to a surface area of said perforated body, is 30% or more.

8. The fiber accumulating apparatus for an absorbent body of an absorbent article according to claim 5, wherein the shape of each of said sucking pores is a conic, pyramidal or funnel shape.

9. The fiber accumulating apparatus for an absorbent body of an absorbent article according to claim 5, wherein the sucking pores are arranged alternately, in a lattice or in a grid.

10. A method for manufacturing an absorbent body of an absorbent article, wherein the fiber accumulating apparatus for an absorbent body of claim 5 is used.

11. The fiber accumulating apparatus for an absorbent body of an absorbent article according to claim 3, wherein a height of the convex member is greater than a depth of said concave portion.

12. The fiber accumulating apparatus for an absorbent body of an absorbent article according to claim 3, wherein the convex member is non-air-permeable.

\* \* \* \* \*